United States Patent
Mehling et al.

(10) Patent No.: US 12,036,852 B2
(45) Date of Patent: Jul. 16, 2024

(54) FABRIC TOP FOR A CONVERTIBLE VEHICLE AND CONVERTIBLE VEHICLE

(71) Applicant: Bayerische Motoren Werke Aktiengesellschaft, Munich (DE)

(72) Inventors: Ralf Mehling, Munich (DE); Daniel Seiboth, Odelzhausen (DE); Erik Seiferling, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 935 days.

(21) Appl. No.: 16/971,882

(22) PCT Filed: Feb. 8, 2019

(86) PCT No.: PCT/EP2019/053073
§ 371 (c)(1),
(2) Date: Aug. 21, 2020

(87) PCT Pub. No.: WO2019/162103
PCT Pub. Date: Aug. 29, 2019

(65) Prior Publication Data
US 2021/0101458 A1   Apr. 8, 2021

(30) Foreign Application Priority Data
Feb. 23, 2018   (DE) .......... 10 2018 202 773

(51) Int. Cl.
*B60J 7/12*   (2006.01)
*B32B 5/02*   (2006.01)
(Continued)

(52) U.S. Cl.
CPC ............. *B60J 7/1226* (2013.01); *B32B 5/022* (2013.01); *B32B 5/08* (2013.01); *B32B 5/18* (2013.01);
(Continued)

(58) Field of Classification Search
CPC ......... B60J 7/12; B60J 7/12226; B32B 5/022; B32B 5/18; B32B 5/245; B32B 5/26;
(Continued)

(56) References Cited

U.S. PATENT DOCUMENTS

| 6,618,944 B1 | 9/2003 | Persson et al. |
| 6,871,898 B2 * | 3/2005 | Jarrard ................ B60J 7/1226 |
| | | 296/107.01 |
| 2009/0286439 A1 | 11/2009 | Wittenzellner et al. |

FOREIGN PATENT DOCUMENTS

| DE | 10 2006 044 234 B4 | 6/2008 |
| DE | 10 2008 064 258 A1 | 6/2010 |

(Continued)

OTHER PUBLICATIONS

English translation of DE 10 2012 011 143; retrieved via Patent-Translate located www.epo.org. (Year: 2023).*
(Continued)

*Primary Examiner* — Jason S Daniels
(74) *Attorney, Agent, or Firm* — Crowell & Moring LLP

(57) ABSTRACT

A fabric top for a convertible vehicle includes, in sequence: an outer cover layer, an insulating layer, an absorber layer and an inner cover layer. The absorber layer at 500 hz has an absorption coefficient of 10 to 65%, at 1000 hz has an absorption coefficient of 15 to 110%, at 2000 hz has an absorption coefficient of 33 to 115%, at 4000 hz has an absorption coefficient of 60 to 110% at 8000 hz has an absorption coefficient of 85 to 120%.

17 Claims, 1 Drawing Sheet

(51) Int. Cl.
*B32B 5/08* (2006.01)
*B32B 5/18* (2006.01)
*B32B 5/24* (2006.01)
*B32B 5/26* (2006.01)
*B32B 5/32* (2006.01)
*B32B 25/04* (2006.01)
*B32B 25/08* (2006.01)
*B32B 25/10* (2006.01)
*B32B 25/18* (2006.01)
*B32B 27/08* (2006.01)
*B32B 27/12* (2006.01)
*B32B 27/30* (2006.01)
*B32B 27/36* (2006.01)
*B32B 27/40* (2006.01)
*C12N 7/00* (2006.01)
*C12Q 1/70* (2006.01)
*G01N 33/569* (2006.01)

(52) U.S. Cl.
CPC ............... *B32B 5/245* (2013.01); *B32B 5/26* (2013.01); *B32B 5/32* (2013.01); *B32B 25/042* (2013.01); *B32B 25/08* (2013.01); *B32B 25/10* (2013.01); *B32B 25/18* (2013.01); *B32B 27/08* (2013.01); *B32B 27/12* (2013.01); *B32B 27/308* (2013.01); *B32B 27/36* (2013.01); *B32B 27/40* (2013.01); *C12N 7/00* (2013.01); *C12Q 1/70* (2013.01); *G01N 33/56983* (2013.01); *B32B 2250/05* (2013.01); *B32B 2262/0246* (2013.01); *B32B 2262/0253* (2013.01); *B32B 2262/0261* (2013.01); *B32B 2262/0276* (2013.01); *B32B 2262/0292* (2013.01); *B32B 2266/0242* (2013.01); *B32B 2266/0278* (2013.01); *B32B 2266/06* (2013.01); *B32B 2307/102* (2013.01); *B32B 2307/718* (2013.01); *B32B 2307/732* (2013.01); *B32B 2605/003* (2013.01); *C12N 2760/16121* (2013.01); *C12N 2760/16131* (2013.01); *C12N 2760/16151* (2013.01); *C12N 2760/16221* (2013.01); *C12N 2760/16232* (2013.01); *C12N 2760/16251* (2013.01)

(58) Field of Classification Search
CPC ....... B32B 27/08; B32B 27/12; B32B 27/308; B32B 27/36; B32B 27/40
USPC .................................................. 296/107.09
See application file for complete search history.

(56) References Cited

FOREIGN PATENT DOCUMENTS

| DE | 10 2010 047 857 A1 | 4/2012 | |
|---|---|---|---|
| DE | 20 2012 104 315 U1 | 11/2012 | |
| DE | 10 2012 011 143 A1 | 12/2013 | |
| DE | 102012011142 A1 * | 12/2013 | ............ B60J 7/1226 |
| DE | 10 2013 000 929 A1 | 3/2014 | |
| WO | WO 2008/031425 A1 | 3/2008 | |
| WO | WO 2009/019220 A1 | 2/2009 | |
| WO | WO-2016096975 A1 * | 6/2016 | ............ B32B 27/08 |

OTHER PUBLICATIONS

English translation of Chinese Office Action issued in Chinese Application No. 201980013876.0 dated Jan. 5, 2023 (seven (7) pages).
International Search Report (PCT/ISA/210) issued in PCT Application No. PCT/EP2019/053073 dated Apr. 24, 2019 with English translation (seven pages).
German-language Written Opinion (PCT/ISA/237) issued in PCT Application No. PCT/EP2019/053073 dated Apr. 24, 2019 (seven pages).
German-language Search Report issued in German Application No. 10 2018 202 773.0 dated Jan. 28, 2019 with partial English translation (13 pages).
"Absorptionsgrad α verschiedener Materialien und Oberflächen", Tontechnik-Rechner—sengpielaudio, Internet Archive: Wayback Machine, Apr. 4, 2017, https://web.archive.org/web/20170404133922/http://www.sengpielaudio.com/Rechner-RT60Koeff.htm, two pages.
"Product data sheet, FiberAcoustic 450", Acoustics, Jan. 21, 2013, https://cdn.shopify.com/s/files/1/0660/2023/files/PDS_FiberAcoustic_450.pdf, two pages.

* cited by examiner

FABRIC TOP FOR A CONVERTIBLE VEHICLE AND CONVERTIBLE VEHICLE

BACKGROUND AND SUMMARY OF THE INVENTION

The present invention relates to a fabric top for a convertible vehicle as well as to a convertible vehicle which comprises such a fabric top.

Fabric tops for convertible vehicles are known from the prior art. For example, DE 102013000929 A1 describes a fabric top for an open passenger motor vehicle having an external convertible top fabric having an internal headlining tier for cladding the convertible top fabric toward the interior of the passenger motor vehicle, and having an intermediate tier which is disposed between the convertible top fabric and the headlining tier, wherein the intermediate tier for the acoustic damping of the fabric top has an air-impermeable, acoustically active, coating.

Moreover, DE 202012104315 U1 describes a convertible top covering having a covering external skin, an interior headlining, an insulating layer which is disposed between the covering external skin and the interior headlining, and a noise damping layer which is disposed between the covering external skin and the interior headlining. The noise damping layer is formed from a non-woven tier which is disposed between the covering external skin and the insulating layer and which by way of local fastening regions is fixed to the covering external skin and/or the insulating layer such that the noise damping layer is free of attachment points between the fastening regions. It is disadvantageous in known fabric tops that the latter do not offer sufficient acoustic damping and simultaneously a high level of noise absorption.

Proceeding from this prior art, it is an object of the present invention to provide a fabric top for a convertible vehicle which by virtue of an enhanced noise absorption and an improved acoustic damping enables a high level of acoustic comfort. It is moreover an object of the invention to provide a convertible vehicle having a very high level of acoustic comfort.

The object is achieved by a fabric top which comprises in this sequence: an external convertible top tier, an insulating layer, an absorbent layer, and an internal convertible top tier.

The external convertible top tier herein represents the tier which in the installed state of the fabric top in a convertible vehicle is in contact with the environment of the convertible vehicle. The external convertible top tier is therefore in particular an at least water-repellent, preferably a watertight, covering which repels weather influences and by virtue of an improved vibration behavior acts in a noise-damping manner.

The insulating layer in terms of the details thereof is not limited and contributes toward improving the damping behavior of noises.

The absorbent layer is distinguished by very positive noise-absorbing properties for absorbing noise from the interior of the vehicle. To this end, the absorbent layer at 500 Hz has a coefficient of absorption of 10 to 65%, at 1000 Hz has a coefficient of absorption of 15 to 110%, at 2000 Hz has a coefficient of absorption of 33 to 115%, at 4000 Hz has a coefficient of absorption of 60 to 110%, and at 8000 Hz has a coefficient of absorption of 85 to 120%. Almost all noise prevalent in the vehicle interior can thus be efficiently absorbed.

The internal convertible top tier, the so-called headlining, in the installed state of the fabric top in a convertible vehicle forms the tier of the fabric top that is in contact with the vehicle interior and also represents a visible face. The internal convertible top tier is permeable to sound and does not act as a barrier layer on which the sound waves would be reflected.

The individual tiers of the fabric top according to the invention do not in each case have to completely overlap one another. Rather, it is possible that individual tiers in terms of the planar extent thereof are configured so as to be smaller or larger, or project from other tiers or are recessed in relation to the latter. However, all tiers of the fabric top substantially largely overlap one another.

The fabric top according to the invention by virtue of the structural and functional construction thereof is distinguished by highly noise-damping and in particular also very positive noise-absorbing properties. The fabric top according to the invention, by virtue of the layered construction having a minor number of layers and with very high functionality with a view to optimizing the aero-acoustics, is relatively cost-effective. This however does not preclude that the fabric top can be completed by further tiers, the latter being in particular in the manner of fabrics.

The dependent claims are the subject matter of advantageous refinements and design embodiments of the invention.

According to one advantageous refinement, a carrier layer is disposed between the external convertible top tier and the insulating layer. The carrier layer can in particular be configured as a non-woven, in particular as a needle-bonded non-woven, and/or as a plastics material film, and serves in particular for guaranteeing a sliding behavior in relation to the surrounding layers and in particular in relation to the external convertible top tier.

A non-woven in the context of the present invention is understood to be a planar structure from fibers which are loosely intermingled but are not connected to one another. The strength of a non-woven is based only on the fiber-inherent adhesion.

A bow for erecting the fabric top in a planar manner is furthermore advantageously disposed between the absorbent layer and the internal convertible top tier. The bow is in particular present in the form of one or a plurality of components having a hollow-profile cross section, for example as a flat profile, U-profile, L-profile, as a tubular profile, or as an open profile. A plurality of these components can be suitably connected to one another. This results in a construction in the manner of a linkage which however is not configured over the full area in or on the fabric top. Rather, the bow is disposed in portions in the fabric top.

According to one further advantageous refinement, the external convertible top tier has an area weight in a range from 800 to 1500 g/m$^2$, and in particular in a range from 1100 to 1300 g/m$^2$. On account thereof, the insertion loss of the external convertible top tier can be increased, in particular in high frequency ranges. Alternatively or additionally, a layer thickness of the external convertible top tier is 0.8 to 2 mm, and in particular 1.5 to 1.7 mm. A layer thickness in a range from 1.5 to 1.7 mm has proven particularly advantageous in terms of a very positive shaping capability and a high level of acoustic damping, in particular when the area weight of the external convertible top tier is approximately 1240 g/m$^2$.

Unless otherwise stated, the layer thickness according to the invention is measured in the stacking direction of the individual tiers of the fabric top.

One further advantageous refinement provides that the external convertible top tier comprises a plastics material layer. The plastics material layer in terms of the details thereof is not limited and can in particular comprise an acrylic layer, a butyl rubber layer, a polyethylene terephthalate layer, a chloroprene layer, a TPU layer, a cotton layer, or arbitrary combinations thereof.

For optimizing the damping of noise, the insulating layer has a layer thickness of 4 to 20 mm, and in particular of 7.5 to 8.5 mm.

The insulating layer can be formed from various materials. The insulating layer preferably comprises a foam layer since the acoustic-damping properties of foam materials are particularly efficient. The foam layer is advantageously formed as a polyurethane foam layer. Alternatively or additionally, the insulating layer can comprise plastics material fibers which are selected from polyester, polyether sulfone, polyacrylate, polyamide, and mixtures thereof. The aforementioned fibers herein improve the stability of the insulating layer, this advantageously having a secondary effect in terms of the acoustic damping behavior. Furthermore alternatively or additionally, the insulating layer has a foam area weight of 520 to 2600 g/m$^2$ and/or of 133 to 666 g/m$^2$ (in particular when a non-woven material is used), in particular of 975 to 1190 g/m$^2$ (in particular when a foam is used), and/or of 250 to 283 g/m$^2$ (in particular when a non-woven material is used).

The absorbent layer furthermore advantageously has a layer thickness of 8 to 15 mm, in particular of 10 to 13 mm, and in particular of 11.5 to 12.5 mm, on account of which the noise-absorbing properties of the absorbent layer can be improved. Alternatively or additionally it is advantageous for the absorbent layer to have an area weight in a range from 300 to 600 g/m$^2$, and in particular from 400 to 500 g/m$^2$. If the area weight is between 300 and 600 g/m$^2$, the degree of absorption in the high-frequency range is enhanced, and sound can be very well absorbed. Alternatively or additionally, it is advantageous for the absorbent layer to comprise a foam layer, a perforated absorbent layer, a slotted absorbent layer, or a layer containing plastics material fibers, or combinations thereof, wherein the plastics material fibers are in particular selected from polyester, polyurethane, polypropylene, polyether sulfone, polyacrylate, polyamide, and mixtures thereof. The absorbent layer can moreover also be embodied as multi-layered absorbent, as a so-called multi-layer absorbent, and comprise various types of layer combinations.

Foam layers herein are particularly well suitable for damping and absorbing sound.

A perforated absorbent and a slotted absorbent differ mainly in terms of the shaping of the openings for absorbing sound. These absorbent layers are advantageously formed from plastics material which has corresponding openings. Polypropylene is well suitable as a plastics material.

If the absorbent layer is configured as a layer containing plastics material fibers, the absorbent layer comprises plastics material fibers which are preferably selected from polyester, polyurethane, polypropylene, polyether sulfone, polyacrylate, polyamide, and mixtures thereof, since the plastics material fibers are distinguished by a very positive and dense non-woven formation with a high density such that an area weight in the range from 300 to 600 g/m$^2$ is very readily achievable.

The internal convertible top tier is particularly advantageously configured so as to be open-cell so that sound is not reflected. Open-cell foamed plastics materials are in particular preferable among open-cell convertible top tiers, and the internal convertible top tier herein particularly preferably comprises an open-cell polyurethane foam or a polymethacrylimide foam.

The internal convertible top tier can moreover also comprise a decorative tier which in this instance is provided as a visible tier.

Furthermore according to the invention, a convertible vehicle which is in particular configured as a convertible motor vehicle and which comprises a fabric top as has been disclosed above is also described. The convertible vehicle, by virtue of the use of the fabric top according to the invention, is distinguished by optimized aero-acoustics by virtue of a very positive absorption of sound in the interior of the convertible vehicle such that an optimized aero-acoustic level is achieved in the interior of the convertible vehicle. The level of noise comfort of the convertible vehicle according to the invention is thus optimal by virtue of the very positive passive acoustics.

The convertible vehicle preferably comprises a fabric top having at least one transparent glass, which forms in particular a rear glass of the convertible vehicle, so that the convertible vehicle also enables a very good circumferential visibility.

The advantages, advantageous effects, and refinements described in the context of the fabric top according to the invention also apply to the convertible vehicle according to the invention.

Further details, features, and advantages of the invention are derived from the description hereunder and from the figures.

DETAILED DESCRIPTION OF THE DRAWINGS

Only those features of the fabric top according to the invention that are relevant to the invention are illustrated in the figures. All other features have been omitted for the sake of clarity.

Figure 1:
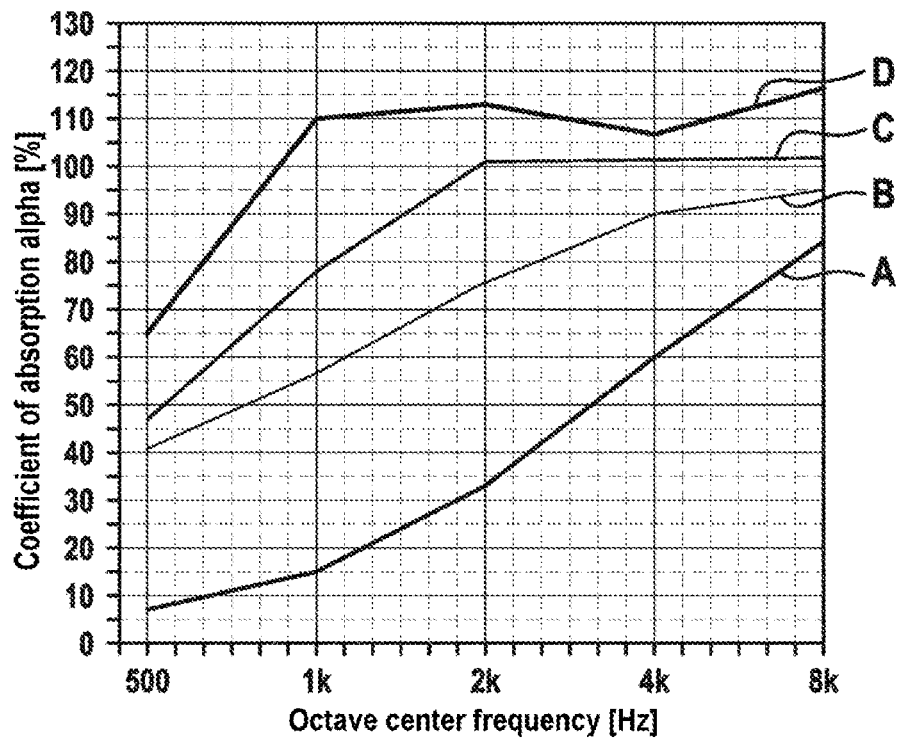
FIG. 1 is a diagram visualizing coefficients of absorption as a function of the octave center frequency.

In detail, FIG. 1 shows a diagram in which coefficients of absorption of materials A, B, C and D are plotted as a function of the octave center frequency. An octave center frequency herein is understood to be a frequency band which has been divided into octaves bands and one-third octaves bands or ⅓ octave bands, respectively which are characterized by (upper and lower) base frequencies and center frequencies. The data was determined using DIN EN ISO 354 (2003.12), DIN ISO 9613-2 (1999.10), DIN EN 61260 (2014.10), and DIN 50014 (1985.07).

The area weights and layer thicknesses of materials A to D herein were as follows:

| Material | Area weight in g/m$^2$ | Layer thickness in mm |
|---|---|---|
| A | 450 | 12 |
| B | 150 | 12 |
| C | 200 | 21 |
| D | 300 | 25 |

By virtue of the absorption behavior in the stated frequency range all four materials A, B, C, and D were able to qualify for use as an absorbent layer in the fabric top according to the invention. To the extent that a material is desired in particular for absorption in the low-frequency range, materials C and D are particularly suitable.

Figure 2:
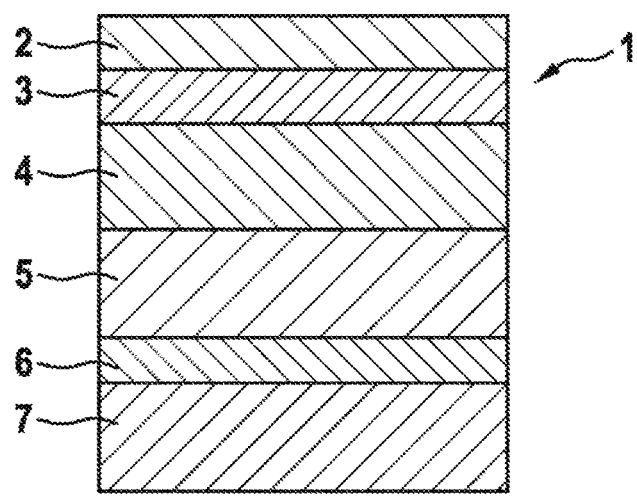
FIG. 2 is a schematic sectional view of a layered construction of a fabric top according to one embodiment of the invention.

FIG. 2 shows a fabric top 1 for a convertible vehicle, and in particular the tiered construction, or the tiered arrangement, respectively, of said fabric top 1 in a sectional view.

The fabric top 1 has an external convertible top tier 2 which has an area weight of 1100 to 1300 g/m², in particular of 1450 g/m², and a layer thickness of 1.5 to 1.7 mm. the external convertible top tier 2 is in particular a laminate which comprises a butyl rubber layer which on both sides is surrounded by two acrylate layers. The external convertible top tier 2 forms the outermost layer of the fabric top 1 which in the installed state in a convertible top for a convertible vehicle comes into contact with the environment of the convertible vehicle.

A tier of a carrier layer 3 adjoins the external convertible top tier 2. The carrier layer 3 is configured in the form of a non-woven and guarantees a sliding behavior in relation to the surrounding layers, in particular in relation to the external convertible top tier 2.

The insulating layer 4 has a layer thickness of 4 to 20 mm and is either configured as a foam layer (in particular polyurethane foam) or comprises plastics material fibers from polyester, polyether sulfone, polyacrylate, polyamide, and mixtures thereof.

The fabric top 1 furthermore comprises an absorbent layer 5. The absorbent layer 5 at 500 Hz has a coefficient of absorption of 10 to 65%, at 1000 Hz has a coefficient of absorption of 15 to 110%, at 2000 Hz has a coefficient of absorption of 33 to 115%, at 4000 Hz has a coefficient of absorption of 60 to 110%, and at 8000 Hz has a coefficient of absorption of 85 to 120%, and has in particular a layer thickness of 11.5 to 12.5 mm, and an area weight in a range from 400 to 500 g/m², so that a very good absorption of noise is achieved in particular in the high-frequency range. The absorbent layer 5 comprises in particular a foam layer, a perforated absorbent layer, a slotted absorbent layer, or a layer containing plastics material fibers, and combinations thereof, wherein the plastics material fibers are in particular selected from polyester, polyurethane, polypropylene, polyether sulfone, polyacrylate, polyamide, and mixtures thereof.

Reference sign 6 represents a bow which is in particular present as a bar-assembly construction. The bow 6 serves for erecting and stabilizing the fabric top 1.

An internal convertible top tier 7 is furthermore disposed below the bow 6. The internal convertible top tier 7 in the installed state of the fabric top 1 in a convertible vehicle faces the interior of the convertible vehicle and is in particular visible in the interior. The internal convertible top tier 7 comprises in particular an open-cell foamed plastics material which comprises polyurethane or polymethacrylimide. On account thereof, the high requirements set in terms of the functional demands with a view to avoiding the reflection of sound can be met.

On account of the tiered arrangement and design embodiment of the individual tiers that form the fabric top 1, a fabric top which is distinguished by very good noise-damping as well as noise-absorbing properties is obtained.

LIST OF REFERENCE SIGNS

1 Fabric top
2 External convertible top tier
3 Carrier layer
4 Insulating layer
5 Absorbent layer
6 Bow
7 Internal convertible top tier

What is claimed is:

1. A fabric top for a convertible vehicle, comprising in sequence:
   an external convertible top tier;
   an insulating layer;
   an absorbent layer; and
   an internal convertible top tier;
   wherein the absorbent layer at 500 Hz has a coefficient of absorption of 25 to 65%, at 1000 Hz has a coefficient of absorption of 15 to 110%, at 2000 Hz has a coefficient of absorption of 33 to 115%, at 4000 Hz has a coefficient of absorption of 60 to 110%, and at 8000 Hz has a coefficient of absorption of 85 to 120%.

2. The fabric top according to claim 1, wherein
   a carrier layer is disposed between the external convertible top tier and the insulating layer, wherein the carrier layer comprises a non-woven or a plastics material film.

3. The fabric top according to claim 2, wherein
   a bow is disposed between the absorbent layer and the internal convertible top tier.

4. The fabric top according to claim 1, wherein
   a bow is disposed between the absorbent layer and the internal convertible top tier.

5. The fabric top according to claim 1, wherein
   the external convertible top tier has at least one of:
   an area weight in a range from 800 to 1500 g/m2, and
   a layer thickness of 0.8 to 2 mm.

6. The fabric top according to claim 5, wherein
   the area weight is from 1100 to 1300 g/m2, and
   the layer thickness is 1.5 to 1.7 mm.

7. The fabric top according to claim 1, wherein
   the external convertible top tier comprises a plastics material layer.

8. The fabric top according to claim 7, wherein
   the plastic material layer is an acrylic layer, a butyl rubber layer, a polyethylene terephthalate layer, a chloroprene layer, a TPU layer, a cotton layer, and arbitrary combinations thereof.

9. The fabric top according to claim 1, wherein at least one of:
   the insulating layer has a layer thickness of 4 to 20 mm,
   the insulating layer comprises a foam layer,
   the insulating layer comprises plastics material fibers which are selected from polyester, polyether sulfone, polyacrylate, polyamide, and mixtures thereof, and
   the insulating layer has a foam area weight of 520 to 2600 g/m2 or of 133 to 666 g/m2.

10. The fabric top according to claim 1, wherein at least one of:
    the insulating layer has a layer thickness of 7.5 to 8.5 mm,
    the insulating layer comprises a polyurethane foam layer,
    the insulating layer comprises plastics material fibers which are selected from polyester, polyether sulfone, polyacrylate, polyamide, and mixtures thereof, and
    the insulating layer has a foam area weight of 975 to 1190 g/m2, or of 250 to 283 g/m2.

11. The fabric top according to claim 1, wherein at least one of:
    the absorbent layer has a layer thickness of 8 to 15 mm,
    the absorbent layer has an area weight in a range from 300 to 600 g/m2, and the absorbent layer comprises a foam layer, a perforated absorbent layer, a slotted absorbent layer, or a layer containing plastics material fibers, or combinations thereof, wherein the plastics material fibers are selected from polyester, polyurethane, polypropylene, polyether sulfone, polyacrylate, polyamide, and mixtures thereof.

12. The fabric top according to claim 11, wherein at least one of:
the absorbent layer has a layer thickness of 10 to 13 mm,
the absorbent layer has an area weight in a range from 400 to 500 g/m2.

13. The fabric top according to claim 1, wherein
the internal convertible top tier is open-cell, and comprises an open-cell foamed plastics material.

14. The fabric top according to claim 13, wherein
the open-cell foamed plastics material is an open-cell polyurethane foam or polymethacrylimide foam.

15. A convertible vehicle, comprising the fabric top according to claim 1.

16. The convertible vehicle according to claim 15, wherein the fabric top comprises at least one transparent glass of the convertible vehicle.

17. The convertible vehicle according to claim 16, wherein
the transparent glass is a rear glass of the vehicle.

* * * * *